US010709800B2

(12) United States Patent
Chowdhary et al.

(10) Patent No.: US 10,709,800 B2
(45) Date of Patent: Jul. 14, 2020

(54) RADIO-OPAQUE WRITING INSTRUMENTS AND METHODS OF USE

(71) Applicants: Prataprai R. Chowdhary, South Jordan, UT (US); Ashok Khandkar, Salt Lake City, UT (US)

(72) Inventors: Prataprai R. Chowdhary, South Jordan, UT (US); Ashok Khandkar, Salt Lake City, UT (US)

(*) Notice: Subject to any disclaimer, the term of this patent is extended or adjusted under 35 U.S.C. 154(b) by 0 days.

(21) Appl. No.: 16/103,870

(22) Filed: Aug. 14, 2018

(65) Prior Publication Data

US 2019/0046666 A1 Feb. 14, 2019

Related U.S. Application Data

(60) Provisional application No. 62/545,478, filed on Aug. 14, 2017.

(51) Int. Cl.
*B43K 29/00* (2006.01)
*A61K 49/04* (2006.01)
*A61B 90/00* (2016.01)
*B43K 5/00* (2006.01)
*B43K 8/14* (2006.01)

(52) U.S. Cl.
CPC .......... *A61K 49/0404* (2013.01); *A61B 90/39* (2016.02); *A61K 49/04* (2013.01); *A61K 49/0409* (2013.01); *A61K 49/0447* (2013.01); *B43K 5/00* (2013.01); *B43K 8/14* (2013.01); *A61B 2090/395* (2016.02); *A61B 2090/3933* (2016.02); *A61B 2090/3966* (2016.02)

(58) Field of Classification Search
CPC ............ A61K 49/0409; A61K 49/0447; A61B 90/39; A61B 2090/3966; A61B 2090/395; A61B 2090/3933
USPC ........................................................ 401/195
See application file for complete search history.

(56) References Cited

U.S. PATENT DOCUMENTS

| 4,813,062 | A | * | 3/1989 | Gilpatrick | ............... A61F 13/44 |
| | | | | | 250/302 |
| 6,972,022 | B1 | | 12/2005 | Griffin | |
| 9,861,449 | B2 | * | 1/2018 | O'Neill, III | ........... A61B 90/39 |
| 9,980,784 | B2 | * | 5/2018 | Fasolino | ................ A61B 90/39 |
| 10,004,843 | B2 | | 6/2018 | Hamilton et al. | |

(Continued)

FOREIGN PATENT DOCUMENTS

JP H01-130997 A 5/1989

*Primary Examiner* — Jennifer C Chiang
(74) *Attorney, Agent, or Firm* — Durham Jones & Pinegar, P.C., Intellectual Property Law Group

(57) ABSTRACT

A radio-opaque composition is formulated to enable a clinician to apply custom markings to a surface, such as a patient's skin or a surgical drape on the patient. More specifically, the radio-opaque composition may be used to write on the surface. The markings may be well-defined and contrast with the surface to which they are applied. Such a composition may include a liquid radio-opaque component that includes one or more radio-opaque materials that have been dissolved in a solvent, as well as a solid radio-opaque component with particles of one or more radio-opaque materials dispersed throughout a carrier, such as the solvent of the liquid radio-opaque component. Marking apparatuses that may be used to write with the radio-opaque composition are also disclosed, as are methods for using the radio-opaque composition.

20 Claims, 3 Drawing Sheets

(56) References Cited

U.S. PATENT DOCUMENTS

| | | |
|---|---|---|
| 2004/0127824 A1 | 7/2004 | Falahee |
| 2005/0261639 A1 | 11/2005 | Herweck |
| 2008/0009718 A1 | 1/2008 | Zohman |
| 2011/0097134 A1* | 4/2011 | Allen ..................... B43K 7/00 401/23 |
| 2016/0346059 A1 | 12/2016 | McNeely |
| 2019/0015174 A1 | 1/2019 | Jones |

* cited by examiner

RADIO-OPAQUE WRITING INSTRUMENTS AND METHODS OF USE

CROSS-REFERENCE TO RELATED APPLICATION

A claim for priority to the Aug. 14, 2017 filing date of U.S. Provisional Application No. 62/545,478, titled RADIO OPAQUE WRITING INSTRUMENTS AND METHODS OF USE ("the '478 Provisional Application"), is hereby made pursuant to 35 U.S.C. § 119(e). The entire disclosure of the '478 Provisional Application is hereby incorporated herein.

TECHNICAL FIELD

This disclosure relates generally to writing instruments and, more specifically, to radio-opaque writing instruments that include a radio-opaque writing medium that is also visible in normal light, non-toxic, biocompatible, antiseptic, and that may be sterile or capable of being sterilized. This disclosure also relates to medical procedures that include applying radio-opaque markings, including, but not limited to, writing radio-opaque markings, on the exterior of a patient, or any covering over a patient.

BACKGROUND

A variety of state-of-the-art medical procedures are conducted in connection with imaging. Common imaging modalities include x-ray, CT (computed tomography), MRI (magnetic resonance imaging), and ultrasound. Imaging may enable a clinician, such as a surgeon, to visualize features inside of a patient's body without requiring the clinician to make large incisions in the patient's body and, thus, "open the body up." Thus, imaging may enable the clinician to conduct less invasive procedures on patients, including so-called "minimally invasive" procedures.

In one example of a minimally invasive procedure—image-guided radiation therapy (IGRT)—real-time imaging is used to precisely deliver radiation therapy to tumors. IGRT uses orthogonal x-rays to visualize one or more radio-opaque fiducial markings on the skin adjacent to the tumor or implanted within soft tissue adjacent to the tumor. These radio-opaque markings act as aids for real-time tracking of the radiotherapy beam during the treatment cycle. Radiation therapy can be delivered in a single dose (i.e., in one single procedure) or in up to five (5) doses. A robotic system delivers highly focused radiation from a single, highly collimated beam from hundreds of angles.

Minimally invasive procedures have also become an essential part of modern surgical techniques with enormous benefits to healthcare including: (a) increased safety to patients resulting from smaller incisions, with less trauma and far less blood loss; (b) decreased scarring, with typical incisions requiring one or two stitches or staples to close the surgical wound; (c) faster recovery, with patients often being discharged the same day and requiring one to two weeks of recovery compared to those with traditional surgeries typically requiring six to eight weeks; and (d) decreased length of hospital stay, with patients being discharged within a twenty-three (23) hour period or scheduled for outpatient surgery, resulting in a significant cost savings.

The success of many modern minimally invasive procedures requires that the treatment (e.g., surgery, beam placement, etc.) be targeted to a precise location within the patient's body. Stringent requirements have been placed on the accuracy of targeting of minimally invasive treatments to prevent the inadvertent performance of a procedure at the wrong site.

Imaging is used in conjunction with a variety of minimally invasive surgical procedures. For example, endovascular treatments, such as the treatment of peripheral arterial disease (PAD), involves image-guided endovascular intervention. PAD affects over 8 million Americans with significant associated morbidity and mortality, with about 2 million revascularizations, bypasses, arthrectomies, and angioplasty procedures being performed annually. Given the success of such procedures, physicians now advocate an "endovascular first" strategy.

As another example, imaging is used in connection with percutaneous biopsies, a rapidly growing common procedure in oncology. Minimally invasive spine surgery is performed to stabilize the vertebral bones and spinal joints and/or relieve pressures applied to the spinal nerves—often as a result of conditions such as a spinal instability, bone spurs, herniated discs, scoliosis or spinal tumors. As small, undetected movements of a patient can result in catastrophic injury to the patient, precise treatment is extremely important. In addition to the foregoing, the use of minimally invasive procedures continues to increase in a variety of specialties, including, but not limited to, neurovascular, gynecological, electrophysiological, orthopedic, and critical care procedures.

Surgical errors in which a surgeon performs the incorrect procedure, operates at the wrong site, or operates on the wrong patient are likely the third leading cause of death in the United States of America. It is believed that these types of surgical errors, which may occur in operating rooms and a variety of other settings (e.g., special procedures units, endoscopy units, interventional radiology suites, etc.) are currently responsible for about 400,000 deaths in the U.S. each year. Wrong site surgery is widely regarded as the most common of these types of surgical errors. In response, the Joint Commission published a Universal Protocol for Preventing Wrong Site, Wrong Procedure, and Wrong Person Surgery, which places emphasis on marking of the incision or insertion site, especially where there is more than one possible location for the procedure, or when performing the procedure would adversely affect patient outcomes and quality of life.

Marking the treatment site is vital to obtaining successful outcomes. Despite the rise in image guided procedures, traditional surgical site marking solutions that remain invisible under fluoroscopic imaging are still being employed. A variety of techniques have been used in an effort to ensure that minimally invasive treatments are properly targeted. Slight movements by the patient (e.g., those caused as the patient breathes, as his or her heart beats, etc.) during IGRT may be accounted for by having the patient wear a special vest that has light-emitting diodes (LEDs) that are detected and tracked by a ceiling-mounted camera array, displayed on a computer monitor, and used to adjust the delivery of radiation according to the patient's respiration or other movements. Thus, the system makes continuous adjustments to deliver the radiation beam to the tumor, allowing for a reduced dose of radiation in treatment margins. While the LEDs enable automated tracking of slight movements by the patient, they may not be visible, or useful as reference points, to a clinician as he or she relies on imaging to conduct a procedure at a particular location. Moreover, the LEDs of such a vest cannot be positioned at specific locations on a patient's body, and they cannot provide customized markings (e.g., fiducial marks, alphanumeric characters, symbols, etc.).

To date, the markers that are available to clinicians for clearly and distinctively marking the skin of patients (e.g., to identify patients, treatment sites, treatment procedures, etc.) are visible to the naked eye, but do not provide any indication of site location and or references to other anatomic landmarks when viewed under common imaging modalities. Moreover, the markings that may be made on a patient with currently available markers do not remain visible after a patient has been covered with drapes or other similar items; thus, concerns of wrong site, wrong patient, and wrong-procedure are not adequately addressed.

In an effort to address these issues, some radio-opaque markings have been developed. These include adhesive radio-opaque markings (i.e., stickers, decals, etc.) with pre-defined elements, such as lines, alphanumeric characters, or arrows or other symbols, that are visible and that may be seen under one or more common types of imaging. While the pre-defined elements may be placed at desired locations on a patient's skin, they do not afford the flexibility of a free-form mark that is versatile and convenient for the clinician in marking.

While the use of radio-opaque marking materials has been suggested, those marking materials suffer from many shortcomings. These shortcomings are largely due to the composition of the radio-opaque marking materials that have been proposed, which are typically thick, are difficult to apply (e.g., by requiring excessive force, because they cannot be applied in a smooth, continuous manner, etc.), and do not remain on the surfaces to which they are applied (e.g., a patient's skin, etc.). The results are easily removable marks of poor definition, limiting the ability of such a radio-opaque material to provide the types of instructions that are useful in properly identifying a patient, a treatment site, and a treatment procedure.

SUMMARY

This disclosure includes compositions and apparatuses for marking a patient's skin or a covering thereon. A marking composition according to this disclosure, which may also be referred to as an "ink," may provide a mark that is visible to an individual when viewed directly and in images obtained from one or more common imaging modalities (e.g., x-ray, CT, ultrasound, etc.). The marking composition may be formulated to enable a clinician to mark a patient's skin clearly and accurately to provide a well-defined and unambiguous marking that contrasts with the surface to which it is applied and that indicates the identity of the patient, the site (e.g., surgical location, etc.) where the patient is to be treated, and/or the procedure, or treatment approach, to be taken, including any patient-specific details of the procedure.

The marking composition may be formulated to resist bleeding when applied to a surface (e.g., a patient's skin, a surgical drape, etc), to dry quickly, and to resist being partially or completely erased (e.g., due to perspiration by the patient; natural oils in or on the patient's skin; fluids, such as skin prep solutions, that are applied to the patient's skin prior to surgery; etc.). The marking composition may be able to resist erasure for a short period of time, for example, several hours, so that markings made by the marking composition remain visible throughout the duration of a particular procedure, or for longer periods of several days in order to facilitate accurate marking visualization for treatments that last for a few days. Such a marking composition may be made from (e.g., comprise, consist essentially of, or consist of) non-toxic and bio-compatible materials, with the essential components of the marking composition comprising its components that are visible to the human eye and its components that are opaque to one or more imaging modalities that are commonly used in medical procedures (e.g., its radio-opaque components, etc.).

In various embodiments, a marking composition according to this disclosure may include binders, radio-opaque particulates, radio-opaque solutions, and a suitable pigment (e.g., dye, etc., such as Gentian violet) that together form a gel or fluid of a viscosity that readily flows and that may be readily applied to a patient's skin and/or to protective plastic surgical films draped over the patient's skin (e.g., after the skin has been prepared with a standard skin prepping solution, such as chlorhexidine, iodine povacrylex combined with isopropyl alcohol, or the like; etc.). More specifically, the marking composition may be formulated for application to a patient's skin and/or to a surgical drape in discrete lines, alphanumeric characters, and/or symbols.

A marking composition according to this disclosure may be delivered via a marking apparatus, such as a writing instrument (e.g., a pen, etc.). The marking apparatus may deliver the marking composition to a surface in a substantially consistent thickness, or it may be configured to deliver the marking material to the surface in a plurality of different thicknesses.

A marking apparatus and/or a marking composition according to this disclosure may be configured to eliminate the tendency of the marking composition to dry out and ruin the marking instrument. More specifically, the marking apparatus and/or the marking composition may be configured to counteract the "gumming up" that may occur when viscous marking compositions that are loaded with high amounts of radio-opaque ingredients interact with surgical prep solutions. In a specific, but non-limiting embodiment, the marking apparatus may include a reservoir that holds the marking composition, as well as a re-homogenizer, such as a steel ball (steel is only one material that may be considered for the ball), which can be shaken to re-homogenize the marking composition and to avoid the settling of radio-opaque particulates in the marking composition as the marking apparatus is stored for extended durations of time. The reservoir holding the marking composition may be in fluid communication with and separated from a second chamber, which may include a nozzle or an orifice with a fixed or adjustable opening, through which the marking composition can be dispensed in a controlled width and thickness.

In another aspect, this disclosure includes methods for performing medical procedures and clinical treatments in which one or more radio-opaque markings are applied to a surface of or associated with a patient undergoing the procedure or treatment.

In one aspect, a method for identifying an entry point for a minimally invasive medical procedure includes applying a radio-opaque marking to an exterior surface on a patient's body, such as his or her skin. Such a technique may be useful in a variety of minimally invasive medical procedures, including, without limitation, laparoscopic surgical procedures, interventional radiology procedures, and catheterization procedures.

In a specific, but non-limiting embodiment, the marking composition may be drawn onto the exterior surface of the patient's body with a marking apparatus according to this disclosure. Alternatively, a radio-opaque decal may be applied to the exterior surface. Such a method may include identifying an estimated entry point for at least one instrument to be inserted into a patient's body during the minimally invasive medical procedure, placing a radio-opaque marking on the estimated entry point, and radiographically imaging a general location of the patient's body where the at least one instrument is to be introduced into the patient's body. In addition to imaging the radio-opaque marking and the estimated entry point and radiographically identifying an actual entry point, the radiographic imaging enables a clinician, such as a doctor, a physician's assistant, or a nurse, to determine an orientation of the actual entry point relative to the radio-opaque marking and a distance between the actual entry point and the radio-opaque marking. With this information, the clinician may identify and, optionally, mark a location of the actual entry point relative to the location that has been marked. Optionally, the foregoing processes may be repeated to further pinpoint the actual entry point. Once a location of the actual entry point is known, a clinician may then make an incision at that location and introduce the at least one instrument into the incision.

In another aspect, a radio-opaque marking may be applied to an exterior surface of a patient, such as the patient's skin, in a radiation treatment procedure (e.g., a procedure for treating one or more tumors within the patient's body, etc.). When used in such a procedure, the radio-opaque marking may identify a location on the exterior of a patient's body to which focused radiation is to be directed.

The location on the exterior of the patient's body to which the radio-opaque marking is to be applied (i.e., the location onto which focused radiation is to be directed during treatment of a tumor) may be identified by any suitable technique, including, without limitation, the use of a CT simulator. With that location precisely identified, a visible, semi-permanent (i.e., ultimately removable) radio-opaque mark may be applied to that precise location on the exterior of the patient's body. Thereafter, focused radiation may be directed onto the semi-permanent radio-opaque mark to treat a tumor corresponding to the semi-permanent radio-opaque mark. Two or more courses of radiation treatment may be effected using the same semi-permanent radio-opaque mark. The courses of radiation may be delivered on different days from one another. If radiation treatments occur over a long enough period of time, a replacement mark may be applied to the exterior of the patient's body before a previously applied mark is completely removed, or disappears.

In this type of method, one or more radio-opaque markings may be used to confirm that each tumor being considered within a patient's body corresponds to a radio-opaque marking on the exterior of the subject's body. The effectiveness of the radiation treatment at each radio-opaque marking may also be determined by comparing a location or a tumor that corresponds to a particular radio-opaque marking in a newly obtained radiographic image to a location or a tumor that corresponds to the same radio-opaque marking in one or more previously obtained radiographic images.

In another aspect, a radio-opaque marking on the exterior of a patient's body may be used to identify the patient, treatment sites, anatomic landmarks, and/or procedure to be conducted, and to mark devices that assist the clinician in performing the procedure using common imaging modalities. In such a method, a radio-opaque patient identifier (e.g., a name, an identification number, etc.) may be applied (e.g., written onto, transferred to, etc.) to a suitable location on the patient's skin. That location of the patient's body may then be imaged. The radio-opaque patient identifier will appear in the image, enabling a clinician who is viewing the radio-opaque patient identifier to confirm an identity of the patient, the site, and the procedure while the clinician views the radiographic image. Such a radio-opaque marker may also ensure that the radiographic image is placed in the proper patient file. Identifying a patient in this manner may minimize errors, ensuring that a patient is properly diagnosed and treated.

Other aspects, as well as features and advantages of various aspects, of the disclosed subject matter will become apparent to those of ordinary skill in the art through consideration of the ensuing description, the accompanying drawings, and the appended claims.

DETAILED DESCRIPTION

Figure 1:
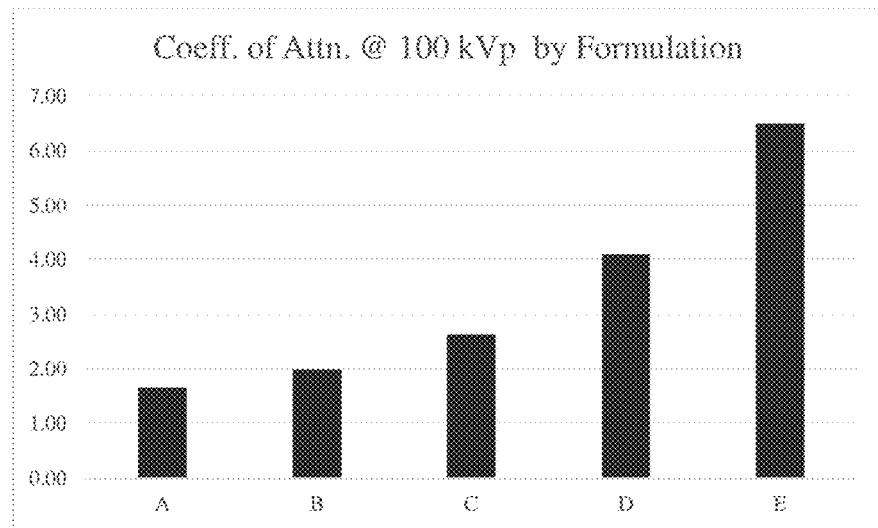
FIG. 1 is a bar graph showing the calculated mass attenuation coefficients of various liquids, including water and various radio-opaque liquid compositions, for radiation at a representative intensity of 100 kVp.

This disclosure is directed to a marking composition and a marking apparatus useful in making clear and unambiguous markings on a patient in preparation for medical procedures, such as minimally invasive surgeries and other procedures. The markings may identify the patient, one or more treatment sites on the patient, the procedure(s) to be conducted at each treatment site (e.g., surgical approaches, etc.), one or more anatomic landmarks, or the like.

A marking composition according to this disclosure may include one or more radio-opaque components. In addition, the marking composition may include a liquid carrier. Optionally (e.g., essentially, non-essentially, etc.), the marking composition may also include a pigment. As another option (e.g., an essential option, a non-essential option, etc.), the marking composition may include one or more of following: thickening agents, cosmetically/dermatologically acceptable vehicles, diluents, carriers, and/or binders.

The liquid carrier of the marking composition may be aqueous or organic, and include one ingredient or a mixture of ingredients. In some embodiments, the liquid carrier may include water and isopropyl alcohol. The isopropyl alcohol may evaporate quickly and, thus, facilitate quick drying of the marking composition once it has been applied to a surface.

The radio-opaque component(s) of the marking composition may also be referred to as "active ingredients." The radio-opaque component(s) may be viewed under one or more imaging modalities (e.g., x-ray, CT, magnetic resonance (MR), ultrasound, etc.) that may be used in conjunction with a medical procedure, as well as one or more components that are visible to an individual without the aid of imaging (i.e., to the "naked eye"). In some embodiments, a radio-opaque component of the marking composition may also be visible to an individual without the aid of imaging. In various embodiments, the marking composition may include a combination of one or more liquid radio-opaque components and one or more solid radio-opaque components. More specifically, the solid radio-opaque component(s) may be carried by (e.g., homogeneously dispersible throughout, etc.) the liquid radio-opaque component(s) and any solvent for the liquid radio-opaque component(s). The combination of liquid and solid radio-opaque components may impart the marking composition with a viscosity suitable for easy flow.

In a specific, but non-limiting, embodiment, the liquid radio-opaque component of a marking composition according to this disclosure may be aqueous or organic. The liquid radio-opaque component (e.g., a solvent of the liquid radio-opaque component, etc.) may comprise the carrier of the marking composition. A liquid radio-opaque component may include a radio-opaque material that has been dissolved in a solvent. Examples of aqueous liquid radio-opaque components include, but are not limited to, potassium iodide solution and iodine solution. The inclusion of iodine in the marking composition may impart the marking composition with antiseptic properties. In addition, the iodide and/or iodine may impart the marking composition with a visible color (i.e., orange-brown to violet), making the marking composition visible even without the addition of a pigment. Examples of organic radio-opaque substances that may be used as the liquid radio-opaque component or in the liquid radio-opaque component include, but are not limited to, iohexol and iopamidol.

Particles of the solid radio-opaque component may be dispersible or dispersed throughout a carrier, such as the solvent for the liquid radio-opaque component or a separate carrier of the marking composition. Particles of the solid radio-opaque component may have sizes that enable the solid radio-opaque composition to remain in suspension throughout the marking compositions. In various embodiments, the particles of the solid radio-opaque component may have sizes of about 2 microns to about 100 microns. The solid radio-opaque component may include one or more pure elements, oxides of elements, and/or salts of elements that are visible under x-ray and under CT imaging. Such an element or elemental species may have an atomic number sufficient to render the solid radio-opaque component radio-opaque under one or more types of imaging commonly used in medical settings (e.g., x-ray, CT, etc.) (e.g., an atomic number of 56 or greater, etc.). Non-limiting examples of such elements or elemental species include barium (Ba) species, bismuth (Bi) species and lanthanum (La) species. Specific examples of such inorganic salts include, but are not limited to, barium salts (e.g., barium sulfate ($BaSO_4$), which is known to be safe and non-toxic to humans), bismuth salts (e.g., bismuth oxide ($Bi_2O_3$)), tungsten salts (e.g., tungsten oxide ($WO_3$)), other salts of elemental species that have high atomic numbers, and combinations thereof. Specific embodiments of metals that may be used as a solid radio-opaque component of the marking composition include, without limitation, tungsten, bismuth, and gold.

Each radio-opaque component of a marking composition according to this disclosure may be included in an amount equal to 0% of the weight of the marking composition to 100% of the weight of the marking composition. That is, the marking composition may include one radio-opaque component that makes up part or all of the marking composition or it may include a combination of radio-opaque components that together may make up part of the marking composition or an entirety of the marking composition. The marking composition may comprise or consist of (a) radio-opaque substance(s) that is (are) non-toxic and biocompatible.

In a specific embodiment, a marking composition may include a carrier that comprises water and isopropyl alcohol, a liquid radio-opaque component that comprises potassium iodide and iodine, and a solid radio-opaque component that includes barium sulfate and bismuth oxide. Particles of the solid radio-opaque component may be dispersible or dispersed throughout the liquid radio-opaque component; thus, the liquid radio-opaque component may function as a carrier of the marking composition. Optionally, the marking composition may also include a pigment, such as Gentian violet. In some embodiments, the marking composition may consist essentially of the carrier, the liquid radio-opaque component, and the solid radio-opaque component (i.e., other ingredients, including the pigment, are not essential to enable the marking composition to be used in a manner that forms a uniform marking that can be seen in visible light as well as under one or more imaging modalities that are used in medical settings). In other embodiments, the pigment may be an essential component of the marking composition. In still other embodiments, the marking composition may consist of the carrier, the liquid radio-opaque component, and the solid radio-opaque component or of the carrier, the liquid radio-opaque component, the solid radio-opaque component, and the pigment.

When one or more liquid radio-opaque components are combined with one or more solid radio-opaque components, the combination may provide for a flowable (e.g., low viscosity) marking composition with a desired level of radio-opacity. More specifically, the inclusion of one or more liquid radio-opaque components in the marking composition may minimize solids loading (i.e., the solids content, by weight) of the marking composition, reducing the overall viscosity of the marking composition while reducing the likelihood that the solid radio-opaque component(s) will settle and increasing the stability of the marking composition. A formulation of the marking composition may enable it to flow through an orifice of a marking apparatus (e.g., a pen, etc., with a configuration that enables it to dispense the marking composition in a manner that resembles writing with a conventional writing instrument) and to be readily and effectively applied to human tissue (e.g., skin, etc.) and, optionally, to other surfaces (e.g., the surfaces of surgical drapes, etc.). For instance, the marking composition may have the consistency of a smoothly flowing fluid that may be applied in a continuous film. Such a marking composition may have a viscosity in a range of about 100 centipoise (cP) (e.g., the viscosity of motor oil) to about 100,000 cP (or 1,000 poise (P)) (e.g., about the viscosity of toothpaste). Various examples of viscosities of a marking composition according to this disclosure include viscosities of about 70,000 cP or less, about 50,000 cP or less, about 30,000 cP or less, about 10,000 cP or less, about 5,000 cP or less, about 2,500 cP or less, about 1,000 cP or less, and about 500 cP or less.

Furthermore, a combination of various radio-opaque components with one another may increase the attenuation coefficient of the marking composition, providing for higher definition imaging contrast than is currently available with radio-opaque marking compositions. The use of two or more radio-opaque components in the marking composition may significantly widen the range of photon energies that are used in clinical imaging and that may be absorbed and, thus, attenuated by the marking composition. Thus, the marking composition may be useful with a variety of imaging conditions or modalities.

To illustrate the effects of using a combination of liquid and solid radio-opaque components, the mass attenuation coefficient of a specific embodiment of marking composition was compared with the mass attenuation coefficients of other substances. In particular, mass attenuation coefficients were determined for: (A) water (to provide a baseline; (B) water with 2% iodine, by weight; (C) water with 2% iodine, by weight, and 5% potassium iodide, by weight; (D) water with 2% iodine, by weight, 5% potassium iodide, by weight, and 13% barium sulfate, by weight; and (E) water with 2% iodine, by weight, 5% potassium iodide, by weight, 13% barium sulfate, by weight, and 5% bismuth oxide, by weight. The mass attenuation coefficients that were calculated cover photon energies applicable to typical diagnostic x-ray and CT imaging (from 1 keV to 0.1 MeV), approach the lower limit of therapeutic radiation, and are taken from the photon interaction database at the National Institute of Standards and Technology and based on the calculations by Seltzer, as described in Radiation Research 136, 147 (1993). The chart of FIG. 1 shows the mass attenuation coefficient for each composition at a representative intensity of 100 kVp. As further radio-opaque components are added, the mass attenuation coefficient increases progressively. This phenomenon is consistent across all energy levels.

By comparison, if barium sulfate is used alone to attain the equivalent level of attenuation achieved from formulation (D) above, which has a solids loading of 13%, a solids loading of 21.7% barium sulfate, by weight, would be required. Thus, with the inclusion of the liquid radio-opaque components (i.e., iodine solution and potassium iodide solution), the composition may provide the same level attenuation with significantly less (i.e., about 40%) less solids loading. Thus, the combination of liquid and solid radio-opaque elements may enable the formulation of marking compositions that have the same ability to attenuate radiation as existing radio-opaque materials, but with significantly less solids loading. With less solids loading, the marking composition is more stable, with a reduced propensity for solids settling, and able to flow better.

Figure 2:
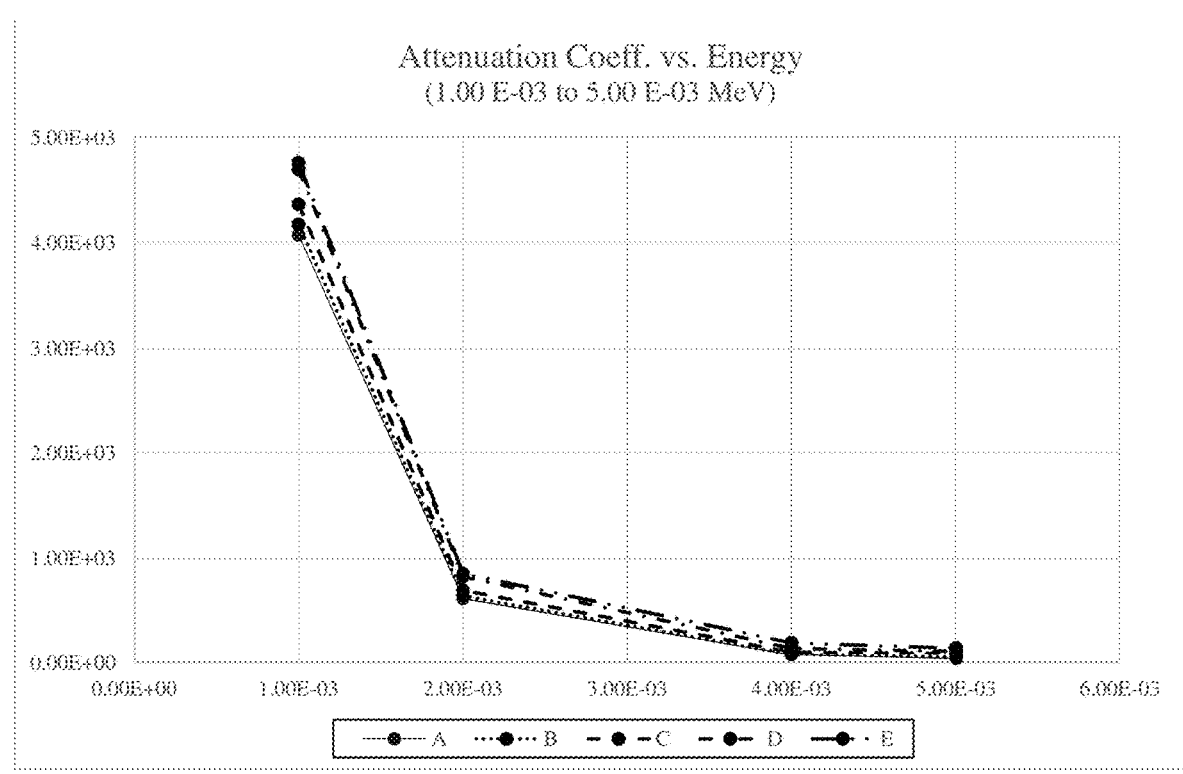
FIGS. 2 and 3 are charts showing the calculated mass attenuation coefficients of the liquids whose mass attenuation coefficients are represented by FIG. 1 at various energies.
Figure 3:
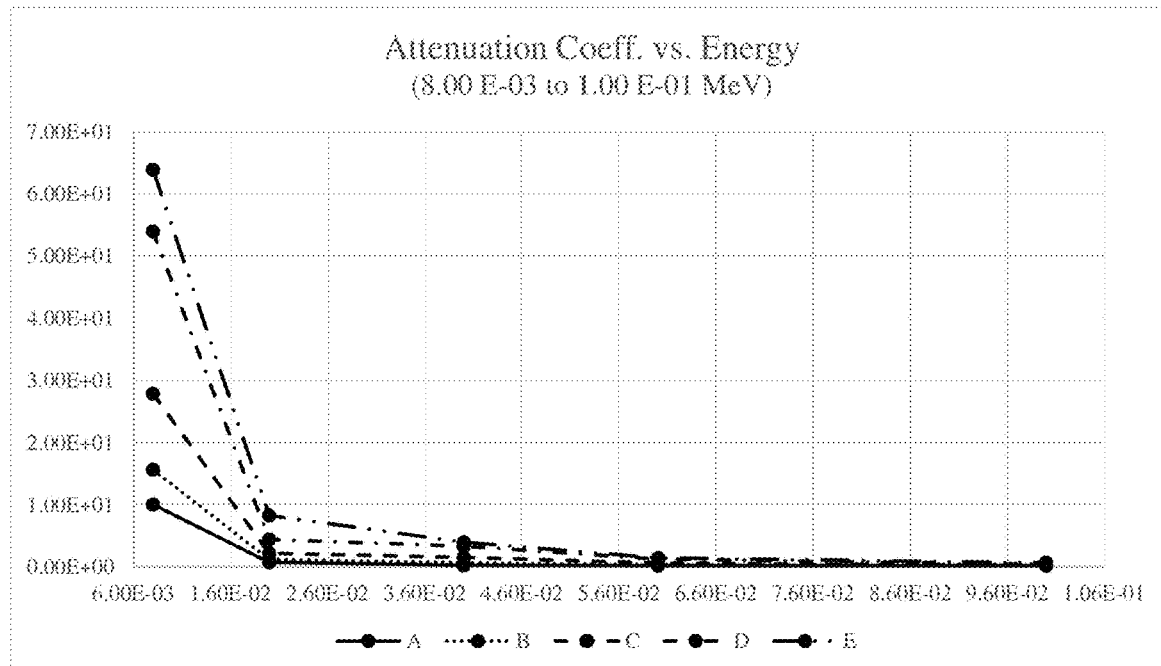

As the charts of FIGS. 2 and 3 show, the mass attenuation coefficient of marking materials with combinations of radio-opaque components increase progressively across all energy levels applicable to typical diagnostic x-ray and CT imaging (i.e., from 1 keV to 0.1 MeV), indicating that the performance of the marking material is consistent and predictable, unlike currently available radio-opaque markers.

In embodiments where the marking composition includes a pigment, the pigment may impart the marking composition with a specific visible color. As a specific, but non-limiting example, the pigment may comprise a dye, such as gentian violet (which is often used to provide pigment for visible medical marking compositions).

In embodiments where the marking composition includes thickening agents, binders, and/or film-forming ingredients, one or more organic and/or inorganic polymers may be included to provide any of these functions. These ingredients may enable tailoring of the viscosity of the marking composition (e.g., they may impart the marking composition with gel-like characteristics, etc.). Such ingredients may be suitable for skin care and/or drug delivery. Examples of film-forming polymers include, but are not limited to, silicones, acrylates, cellulose compounds, polyvinyl alcohol, gelatin, xanthan gum, and polyethylene glycol. The inclusion of one or more film-forming polymers in the marking composition may impart the marking composition with temporary indelible characteristics (e.g., enable a marking to remain on a surface for a particular duration of time, prevent the marking from rubbing off of the surface, etc.).

Figure 4:
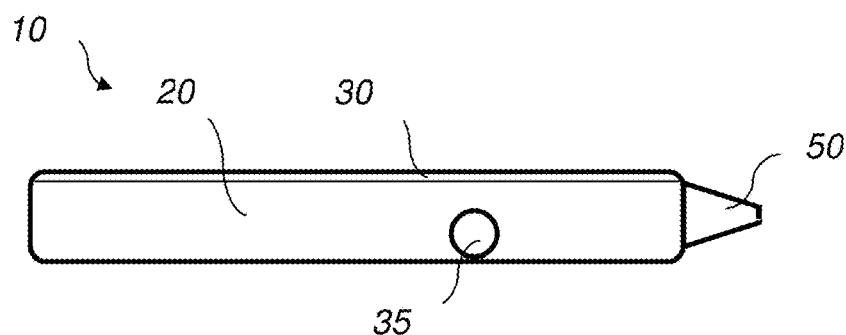
FIGS. 4 and 5 provide schematic representations of embodiments of marking apparatuses.

As illustrated by FIG. 4, an embodiment of a marking apparatus 10 that is capable of dispensing a marking composition 20 may include a reservoir 30 that holds the marking composition 20 and a re-homogenizer 35 (e.g., a steel ball, etc.) that is capable of homogenizing the marking composition 20 in the event that any of the ingredients of the marking composition 20 separate from the remainder of the marking composition 20. In some embodiments, the reservoir 30 of the marking apparatus 10 may be transparent to enable a clinician to visually determine whether the marking composition 20 is homogeneous and able to flow freely. After noting that the marking composition 20 is homogeneous and able to flow freely, the clinician may use the marking apparatus 10 to dispense the marking composition 20 through a dispenser tip 50 that communicates with the reservoir 30 to make markings on a surface.

Figure 5:
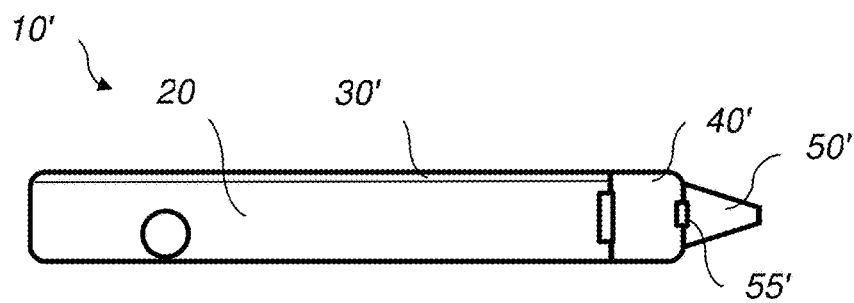

Alternatively, in the embodiment of marking apparatus 10' depicted by FIG. 5, the marking composition 20 may flow from the reservoir 30' into a chamber 40'. The chamber may, in some embodiments, be transparent to enable a clinician to view the marking composition 20 therein. The marking composition 20 may flow from the reservoir 30' to the chamber 40' upon actuating the dispenser 50' of the marking apparatus 10' (e.g., by rotating the dispenser 50', etc.). Such an arrangement may ensure that the reservoir 30' containing the marking composition 20 is not exposed to ambient air and, thus, resists drying prior to being dispensed by the marking apparatus 10'.

As another alternative, also depicted by FIG. 5, the chamber 40' may be maintained under positive pressure and the marking apparatus 10' may include a user-controlled feature 55' (e.g., a valve, etc.) that controls the flow of the marking composition 20 from the chamber 40' to the dispenser 50' and, thus, the flow of the marking composition 20 out of the dispenser 50' and onto a surface.

In some embodiments, the dispenser 50, 50' of a marking apparatus 10, 10' may include an orifice of adjustable size. Such an orifice may enable a user (e.g., a clinician, etc.) to select a desired line width, or thickness, of markings made as the marking composition 20 passes out of the orifice of the dispenser 50, 50'.

Figure 6:
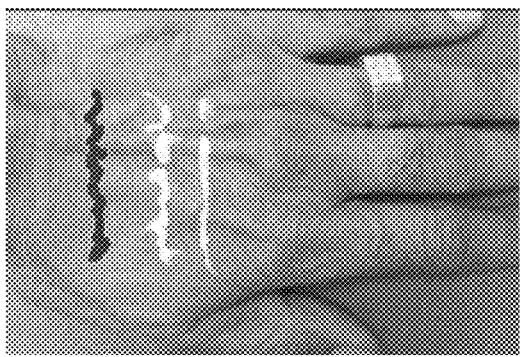
FIG. 6 is a visible image of visible and radio-opaque markings made on an individual's skin with an embodiment of a marking composition according to this disclosure.
Figure 7:
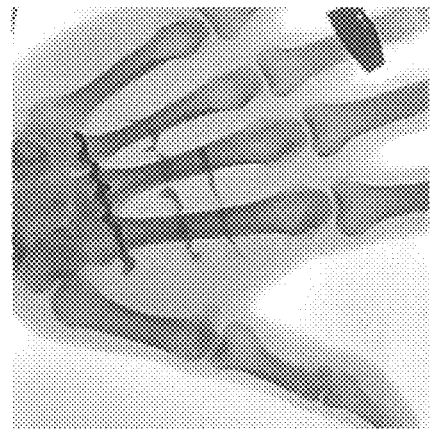
FIG. 7 is a radiographic image of the visible and radio-opaque markings made on the individual's skin with the embodiment of marking composition according to this disclosure.

FIG. 6 is a visible image showing application of a marking composition according to this disclosure to an individual's skin with a marking apparatus according to this disclosure. The first marking (i.e., the marking on the left) is made with a marking composition that includes a pigment, while the second and third markings (i.e., the marking in the center and the marking at the right, respectively) are made with marking compositions that lack pigments. The markings have been defined by marking compositions with different solids loading of radio-opaque material. Each of the markings is clearly visible to the naked eye. FIG. 7 is an x-ray image of the same markings, illustrating that the markings are visible under imaging that is commonly used in medical settings.

A basic embodiment of a method for preparing for surgical procedure, includes providing a marking apparatus 10, 10', making one or more visible and radio-opaque markings on the patient or a covering over the patient with the marking apparatus 10, 10', and subjecting the appropriate site to imaging (e.g., x-ray/fluoroscopy, etc.) for the purpose of comparing the indication to one or more internal structures associated with the procedure. In order to mark at or near the surgical site, the clinician can shake the marking apparatus 10, 10' and observe that the marking composition 20 is able to flow freely, then dispense the marking composition 20 from the dispenser 50, 50' of the marking apparatus 10, 10'. A marking composition according to this disclosure may enable the clinician to make customized, precise markings on the patient and/or on coverings over the patient. The marking may be customized for the patient, and may include information such as the patient's identity, the site where the procedure is to be performed, and information about the procedure to be performed (e.g., to assist in placing surgical instrument access points in the patient which are often necessary in minimally invasive surgical procedures, etc.).

In use, after covering the operative site with the sterile surgical film, the clinician can subject the site to x-ray exposure and, by referring to the marking(s) formed by the radio-opaque composition to ensure that the proper procedure is being conducted at the proper site on the proper patient. In situations when a clinician finds that the first incision marking is not optimal, the marking composition 20 may be removed and an appropriate mark may be made at another location.

By identifying a patient with radio-opaque marking on the patient, images may be accurately matched with the appropriate patient.

Although the foregoing disclosure sets forth many specifics, these should not be construed as limiting the scope of any of the claims, but merely as providing illustrations of some embodiments and variations of elements and/or features of the disclosed subject matter. Other embodiments of the disclosed subject matter may be devised which do not depart from the spirit or scope of any of the claims. Features from different embodiments may be employed in combination. Accordingly, the scope of each claim is limited only by its plain language and the legal equivalents thereto.

What is claimed:

1. A composition for use in marking a surface in connection with an imaging-assisted medical procedure, comprising:
    a first radio-opaque component comprising a first radio-opaque material dissolved in a solvent; and
    a second radio-opaque component comprising a second radio-opaque material dispersed throughout a carrier,
    the first radio-opaque material and the second radio-opaque material comprising different radio-opaque materials with different radio-opaque characteristics.

2. The composition of claim 1, wherein the carrier throughout which the second radio-opaque material is dispersed comprises the solvent within which the first radio-opaque material is dissolved.

3. The composition of claim 1, wherein the first radio-opaque component and the second radio-opaque component are non-toxic.

4. The composition of claim 1, wherein the first radio-opaque material comprises at least one of potassium iodide and iodine.

5. The composition of claim 4, wherein the second radio-opaque material comprises at least one of an element, an oxide of an element, and a salt of an element, with the element having an atomic number of at least 56.

6. The composition of claim 5, wherein the second radio-opaque material comprises at least one barium sulfate, bismuth oxide, and tungsten oxide.

7. The composition of claim 4, wherein the second radio-opaque material comprises at least one of an element, an oxide of an element, and a salt of an element, with the element having an atomic number of at least 56.

8. The composition of claim 7, wherein the second radio-opaque material comprises at least one of barium sulfate, bismuth oxide, and tungsten oxide.

9. The composition of claim 7, wherein the second radio-opaque material comprises at least one of tungsten, bismuth, and gold.

10. The composition of claim 1, further comprising:
    at least one polymer capable of:
        enabling the composition to form a film;
        tailoring a viscosity of the composition; and/or
        rendering the composition at least temporarily indelible.

11. The composition of claim 1, further comprising:
    a pigment capable of imparting the composition with a desired color.

12. The composition of claim 1, having a viscosity of about 100 cP to about 100,000 cP.

13. The composition of claim 1, having a viscosity of about 500 cP or less.

14. The composition of claim 1, comprising:
    a carrier comprising water and isopropyl alcohol;
    with the first radio-opaque component comprising potassium iodide and iodine in solution; and
    with the second radio-opaque component comprising barium sulfate and bismuth oxide.

15. The composition of claim 14, wherein:
    the iodine comprises about 2% of the weight of the composition;
    the potassium iodide comprises about 5% of the weight of the composition;
    the barium sulfate comprises about 15% of the weight of the composition; and
    the bismuth oxide comprises about 5% of the weight of the solution.

16. The composition of claim 14, further comprising: Gentian violet.

17. A radio-opaque writing instrument, comprising:
    a container;
    a radio-opaque marking composition within the container, the radio-opaque marking composition capable of being used to write, the radio-opaque marking composition consisting of non-toxic, biocompatible contents, including:
        a liquid radio-opaque component; and
        a solid radio-opaque component;
    a dispenser capable of delivering the radio-opaque marking composition from the container onto a writing surface.

18. The radio-opaque writing instrument of claim 17, wherein the solid radio-opaque component is dispersed throughout the liquid radio-opaque component.

19. A method for correlating radiographic images to a patient, comprising:
    placing a visible, radio-opaque marking material that includes a liquid radio-opaque component and a solid radio-opaque component on the patient's skin, adjacent to a location of the patient's body to be radiographically imaged; and
    radiographically imaging the location of the patient's body to obtain a radiographic image, the radio-opaque patient identifier appearing in the radiographic image.

20. The method of claim 19, wherein placing the visible, radio-opaque marking material that includes the liquid radio-opaque component and the solid radio-opaque component on the patient's skin comprises placing a marking material that includes the solid radio-opaque component dispersed in the liquid radio-opaque component on the patient's skin.

* * * * *